(12) United States Patent
Stevens et al.

(10) Patent No.: US 10,580,614 B2
(45) Date of Patent: Mar. 3, 2020

(54) COMPRESSIVE SCANNING SPECTROSCOPY

(71) Applicant: Battelle Memorial Institute, Richland, WA (US)

(72) Inventors: Andrew J. Stevens, Richland, WA (US); Libor Kovarik, Pasco, WA (US); Nigel D. Browning, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 243 days.

(21) Appl. No.: 15/482,629

(22) Filed: Apr. 7, 2017

(65) Prior Publication Data

US 2017/0316916 A1  Nov. 2, 2017

Related U.S. Application Data

(60) Provisional application No. 62/330,004, filed on Apr. 29, 2016.

(51) Int. Cl.
*H01J 37/28* (2006.01)
*H01J 37/22* (2006.01)
*H01J 37/244* (2006.01)
*G01N 23/00* (2006.01)

(52) U.S. Cl.
CPC ........... *H01J 37/28* (2013.01); *G01N 23/00* (2013.01); *H01J 37/222* (2013.01); *H01J 37/244* (2013.01); *H01J 2237/221* (2013.01); *H01J 2237/24455* (2013.01); *H01J 2237/24485* (2013.01); *H01J 2237/24578* (2013.01); *H01J 2237/24585* (2013.01); *H01J 2237/2802* (2013.01)

(58) Field of Classification Search
USPC ........................................................ 250/307
See application file for complete search history.

(56) References Cited

U.S. PATENT DOCUMENTS

| | | |
|---|---|---|
| 3,633,037 A | 1/1972 | Langenbeck |
| 5,004,918 A | 4/1991 | Tsuno et al. |
| 5,051,585 A | 9/1991 | Koshishiba et al. |
| 5,258,246 A | 11/1993 | Berger et al. |
| 5,298,747 A | 3/1994 | Ichikawa et al. |
| 5,395,738 A | 3/1995 | Brades et al. |
| 5,401,932 A | 3/1995 | Hashimoto et al. |

(Continued)

FOREIGN PATENT DOCUMENTS

WO  WO 2015/061037  4/2015

OTHER PUBLICATIONS

Llull; et. al., "Coded Aperture Compressive Temporal Imaging", Optics Express, vol. 21, No. 9, 2013 pp. 10526-10545 (Year: 2013).*

(Continued)

*Primary Examiner* — Phillip A Johnston
(74) *Attorney, Agent, or Firm* — Klarquist Sparkman, LLP

(57) ABSTRACT

Mask-modulated spectra are incident to a sensor and are summed during a frame time. After the frame time, a compressed spectrum is read out based on the sum and decompressed to obtain spectra for some or all specimen locations. The mask-modulated spectrum that are summed are associated with different modulations produced by a common mask.

26 Claims, 11 Drawing Sheets

(56) References Cited

U.S. PATENT DOCUMENTS

| | | | |
|---|---|---|---|
| 5,798,524 A * | 8/1998 | Kundmann | H01J 37/05 250/305 |
| 6,124,063 A | 9/2000 | Dauksher | |
| 6,310,341 B1 | 10/2001 | Todokoro et al. | |
| 6,812,473 B1 | 11/2004 | Amemiya | |
| 7,417,227 B2 | 8/2008 | Matsumoto et al. | |
| 7,465,923 B2 | 12/2008 | Nishiumi et al. | |
| 7,825,378 B2 | 11/2010 | Yakushevska et al. | |
| 7,834,795 B1 | 11/2010 | Dudgeon et al. | |
| 7,928,376 B2 | 4/2011 | Kaji et al. | |
| 8,125,549 B2 | 2/2012 | Dekel | |
| 8,190,007 B2 | 5/2012 | Meijer et al. | |
| 8,217,352 B2 | 7/2012 | Reed | |
| 8,334,512 B2 | 12/2012 | Luecken et al. | |
| 8,338,782 B2 | 12/2012 | Luecken et al. | |
| 8,553,994 B2 | 10/2013 | Tian et al. | |
| 8,648,955 B2 | 2/2014 | Kang et al. | |
| 8,725,784 B2 | 5/2014 | Davenport et al. | |
| 8,748,818 B2 | 6/2014 | Own et al. | |
| 8,772,716 B2 | 7/2014 | Buijsse | |
| 8,785,850 B2 | 7/2014 | Malac et al. | |
| 8,829,436 B2 | 9/2014 | Iijima et al. | |
| 8,907,280 B1 * | 12/2014 | Larson | G01N 23/225 250/307 |
| 8,933,401 B1 * | 1/2015 | Reed | H01J 37/28 250/307 |
| 9,040,911 B2 | 5/2015 | Ogashiwa et al. | |
| 9,129,774 B2 | 9/2015 | Buijsse et al. | |
| 9,165,743 B2 | 10/2015 | Reed et al. | |
| 9,412,558 B2 | 8/2016 | Van Dyck et al. | |
| 9,620,330 B2 | 4/2017 | Potocek et al. | |
| 10,170,274 B2 * | 1/2019 | Stevens | H01J 37/222 |
| 2001/0054697 A1 | 12/2001 | Yamashita | |
| 2002/0148962 A1 | 10/2002 | Hosokawa et al. | |
| 2003/0006373 A1 | 1/2003 | Koguchi et al. | |
| 2005/0220266 A1 | 10/2005 | Hirsch | |
| 2006/0239336 A1 | 10/2006 | Baraniuk et al. | |
| 2007/0228277 A1 | 10/2007 | Tsuneta et al. | |
| 2007/0284528 A1 | 12/2007 | Benner et al. | |
| 2008/0203296 A1 | 8/2008 | Terada et al. | |
| 2008/0254376 A1 | 10/2008 | Lin et al. | |
| 2009/0200464 A1 | 8/2009 | Tiemeijer et al. | |
| 2010/0252735 A1 | 10/2010 | Hytch et al. | |
| 2011/0168903 A1 | 7/2011 | Kyele et al. | |
| 2011/0192976 A1 | 8/2011 | Own et al. | |
| 2011/0210249 A1 | 9/2011 | Benner | |
| 2011/0220796 A1 | 9/2011 | Nicolopoulos | |
| 2012/0049060 A1 | 3/2012 | Luecken et al. | |
| 2012/0123581 A1 | 5/2012 | Smilde et al. | |
| 2013/0099115 A1 | 4/2013 | Glaeser et al. | |
| 2013/0126729 A1 | 5/2013 | Own et al. | |
| 2013/0193322 A1 | 8/2013 | Blackburn | |
| 2014/0061463 A1 | 3/2014 | Buijsse et al. | |
| 2014/0138542 A1 | 5/2014 | Inada et al. | |
| 2014/0140375 A1 | 5/2014 | Muqaibel et al. | |
| 2014/0166880 A1 | 6/2014 | Shiue et al. | |
| 2014/0224988 A1 | 8/2014 | Tamaki et al. | |
| 2015/0055745 A1 | 2/2015 | Holzner et al. | |
| 2015/0069233 A1 | 3/2015 | Anderson et al. | |
| 2015/0243474 A1 | 8/2015 | Lazic et al. | |
| 2015/0351705 A1 | 12/2015 | Brady et al. | |
| 2015/0371815 A1 | 12/2015 | Potocek et al. | |
| 2016/0111247 A1 | 4/2016 | Potocek et al. | |
| 2016/0276129 A1 | 9/2016 | Stevens et al. | |
| 2016/0301915 A1 | 10/2016 | Shechtman et al. | |
| 2017/0025247 A1 | 1/2017 | Stevens et al. | |
| 2017/0146787 A1 | 5/2017 | Reed | |

OTHER PUBLICATIONS

Aharon et al., "A: K-SVD: An Algorithm for Designing Overcomplete Dictionaries for Sparse Representation," *IEEE Trans. Signal Process.*, 54:4311-4322 (Nov. 2006).

Arons et al., "Einstein's Proposal of the Photon Concept—a Translation of the Annalen der Physik Paper of 1905," American Journal of Physics, 33(5):367-374 (May 1965).

Baraniuk et al., "A Simple Proof of the Restricted Isometry Property for Random Matrices," *Constructive Approximation*, 28:253-263 (Dec. 2008).

Baraniuk, "Compressive Sensing," *IEEE Signal Process. Mag.*, 24, 9 pages (Jul. 2007).

Binev et al., "Compressed Sensing and Electron Microscopy," Vogt et al. (eds.), *Modeling Nanoscale Imaging in Electron Microscopy, Nanostructure Science and Technology*, Springer, pp. 73-126 (Feb. 2012).

Binev et al., "High-Quality Image Formation by Nonlocal Means Applied to High-Angle Annular Dark-Field Scanning Transmission Electron Microscopy (HAADF-STEM)," Vogt et al. (eds.), *Modeling Nanoscale Imaging in Electron Microscopy. Nanostructure Science and Technology*, Springer, pp. 127-145 (Jan. 2012).

Bioucas-Dias et al., "Two-Step Iterative Shrinkage/Thresholding Algorithms for Image Restoration," *IEEE Trans, Image Process.*, 16:2992-3004 (Nov. 2007).

Brand et al., "Super-resolution in optical data storage." Journal of Optics A: Pure and Applied Optics 1:794-800 (Nov. 1999).

Candès et al., "Uncertainty Principles: Exact Signal Reconstruction from Highly Incomplete Frequency Information," *IEEE Trans, Inform. Theory*, 52:489-509, (Jan. 2006).

Candès, "The Restricted Isometry Property and its Implications for Compressed Sensing," *Comptes Rendus Mathematique*, 346:589-592 (May 2008).

Candès et al., "Towards a Mathematical Theory of Super-resolution." Communications on Pure and Applied Mathematics 67: 906-956 (Jun. 2012).

Chen et al., "Compressive Sensing on Manifolds Using a Nonparametric Mixture of Factor Analyzers: Algorithm and Performance Bounds," IEEE Trans, Signal Process., 58:6140-6155 (Dec. 2010).

DeLaRiva et al., "In-Situ Transmission Electron Microscopy of Catalyst Sintering," Catalysis, 308:291-305 (Sep. 2013).

Donoho, "Compressed Sensing," *IEEE Trans, Inform. Theory*, 52:1289-1306, (Apr. 2006).

Evans et al., "Controlled Growth of Nanoparticles from Solution with In-Situ Liquid Transmission Electron Microscopy," *Nano Lett.* 11:2809-2813 (Jul. 2011).

Fernandez-Granda, "Super-resolution and compressed sensing." SIAM News 46 (Oct. 2013).

Ferreira et al., "In-Situ Transmission Electron Microscopy," *MRS Bull.* 33:83-90 (Feb. 2008).

Foucart et al., "A Mathematical Introduction to Compressive Sensing," Springer, New York, 634 pages (Aug. 2013).

Gatan, "TEM Imaging & Spectroscopy," http://www.gatan.com/products/tem-imaging-spectroscopy, accessed Dec. 19, 2014, 5 pages.

Gershman, et al., "A Tutorial on Bayesian Nonparametric Models," *J. Math. Psychol.* 56:1-12 (Feb. 2012).

Ghahramani et al., "The EM Algorithm for Mixtures of Factor Analyzers," Technical Report CRG-TR-96-1, University of Toronto, 8 pages (May 1996).

Gren et al., "Über einen die Erzeugung and Verwandlung des Lichtes betreffenden heuristischen Gesichtspunkt," Annalen der Physik, 14(S1):164-18 (2005).

Goris et al., "Electron Tomography Based on a Total Variation Minimization Reconstruction Technique," *Ultramicroscopy*, 113:120-130 (Feb. 2012).

Griffiths et al., "The Indian Buffet Process: An Introduction and Review," *J. Mach. Learn. Res.*, 12:1185-1224 (Apr. 2011).

Haider et al., "Towards 0.1 nm Resolution with the First Spherically Corrected Transmission Electron Microscope," *J Electron. Microsc.* (Tokyo), 47:395-405 (Jan. 1998).

He et al., "Face Recognition Using Laplacianfaces," *IEEE Trans, Pattern Anal. Mach. Intell.*, 27:328-340 (Jan. 2005).

Huang et al., "In-Situ Observation of the Electrochemical Lithiation of a Single SnO2 Nanowire Electrode," Science, 330:1515-1520 (Dec. 2010).

International Search Report and Written Opinion from International Application No. PCT/US2016/023286, dated Aug. 5, 2016, 10 pages.

(56) References Cited

OTHER PUBLICATIONS

International Search Report and Written Opinion from International Application No. PCT/US2017/026664, dated Sep. 18, 2017, 15 pages.
Jinschek et al., "Image Resolution and Sensitivity in an Environmental Transmission Electron Microscope," *Micron*. 43:1156-1168 (Nov. 2012).
Jinschek, "Advances in the Environmental Transmission Electron Microscope (etem) for Nanoscale In-Situ Studies of Gas-Solid Interactions," *Chem. Commun.*, 50:2696-2706 (Jan. 2014).
Kanaya et al., "Penetration and energy-loss theory of electrons in solid targets," Journal of Physics D: Applied Physics, 5(1): 43 (Jan. 1972).
Kanaya et al., "Secondary electron emission due to primary and backscattered electrons," Journal of Physics D: Applied Physics, 5(9):1727 (1972).
Kraemer et al., "Ultra high-density optical data storage: information retrieval an order of magnitude beyond the Rayleigh limit." Chemical physics 285: 73-83 (Dec. 2002).
Liao et al., "Generalized Alternating Projection for Weighted-f2,1 Minimization with Applications to Model-Based Compressive Sensing," *SIAM J. Imaging Sci*, 7:797-823 (Apr. 2014).
Llull et al., "Coded Aperture Compressive Temporal Imaging," *Opt. Express*, 21:10526-10545 (Apr. 2013).
Mairal et al., "Sparse Modeling for Image and Vision Processing," arXiv preprint arXiv:1411.3230, 205 pages (Dec. 2014).
McMullan et al., "Comparison of Optimal Performance at 300 keV of Three Direct Electron Detectors for Use in Low Dose Electron Microscopy," *Ultramicroscopy*, 147:156-163 (Dec. 2014).
Mehraeen et al., "A (S)TEM Gas Cell Holder with Localized Laser Heating for In-Situ Experiments," *Microscopy Microanal*, 19:470-478 (Apr. 2013).
Neal, "Markov Chain Sampling Methods for Dirichlet Process Mixture Models," *J. Comput. Graph. Stat.*, 9:249-265 (Feb. 2000).
Nichelatti, et al., "Photoluminescence from colour centres generated in lithium flouride thin films and crystals by extreme-ultraviolet irradiation," Nuclear Intruments and Methods in Physics Research B, 268(19):3035-3059 (May 16, 2010).
Olshausen et al., "Emergence of Simple-Cell Receptive Field Properties by Learning a Sparse Code for Natural Images," *Nature*, 381:607-609 (Jun. 1996).

Potts, "Electron probe microanalysis," A Handbook of Silicate Rock Analysis, Blackie Academy, Chapman & Hall, Chapter 10, pp. 326-382 (1987).
Rasmussen, "The Infinite Gaussian Mixture Model," *in NIPS*, pp. 554-560, Denver, CO (1999).
Saghi et al., "Reduced-Dose and High-Speed Acquisition Strategies for Multi-Dimensional Electron Microscopy," *Adv. Struct. Chem. Imaging*, 10 pages (May 2015).
Seitz, "Color Center in Alkali Halide Crystals," Reviews of Modern Physics, pp. 384-408 (1946).
Stevens et al., "The Potential for Bayesian Compressive Sensing to Significantly Reduce Electron Dose in High-Resolution STEM Images," *Microscopy*, 63:41-51 (Oct. 2013).
Surrey et al., "Quantitative Measurement of the Surface Self-Diffusion on Au Nanoparticles by Aberration-Corrected Transmission Electron Microscopy," *Nano Lett.*, 12:6071-6077 (Nov. 2012).
Tipping et al., "Mixtures of Probabilistic Principal Component Analyzers," *Neural Comput.*, 11:443-482 (1999).
Tipping et al., "Probabilistic Principal Component Analysis," *J. R. Stat. Soc. Series B (Stat. Methodol.)*, 61:611-622 (1999).
Tsyganov et al., "Analysis of Ni Nanoparticle Gas Phase Sintering," *Phys. Rev. B.*, 75, 9 pages (Jan. 2007).
Wakin, Manifold-Based Signal Recovery and Parameter Estimation From Compressive Measurements, arXiv preprint arXiv:1002.1247, 22 pages (Feb. 2010).
Xing et al., "Dictionary Learning for Noisy and Incomplete Hyperspectral Images," *SIAM J. Imaging Sci*. 5:33-56 (Jan. 2012).
Yang et al., "Gaussian Mixture Model for Video Compressive Sensing," *2013 20th IEEE International Conference On Image Processing (ICIP)*, pp. 19-23 (Sep. 2013).
Yoshida et al., "Visualizing Gas Molecules Interacting with Supported Nanoparticulate Catalysts at Reaction Conditions," *Science*, 335:317-319 (Jan. 2012).
Yuan et al., "Adaptive Temporal Compressive Sensing for Video," *2013 20th IEEE International Conference On Image Processing (ICIP)*, Melbourne, Australia, pp. 14-18 (Sep. 2013).
Yuan et al., "Low-Cost Compressive Sensing for Color Video and Depth," *2014 IEEE Conference On Computer Vision and Pattern Recognition (CVPR)*, IEEE, arXiv:1402.6932v1, 8 pages (Jun. 2014).
Zhou et al., "Nonparametric Bayesian Dictionary Learning for Analysis of Noisy and Incomplete Images," *IEEE Trans. Image Process.*, 21:130-144 (Jan. 2012).

* cited by examiner

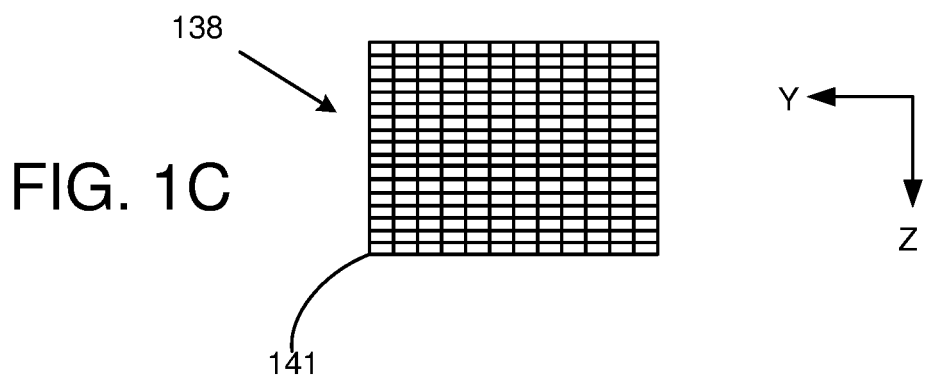
FIG. 1C
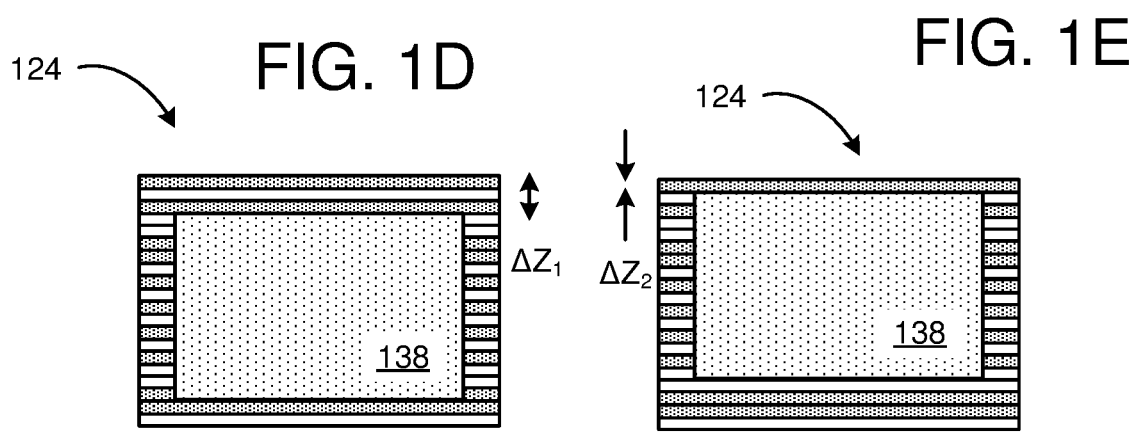
FIG. 1D
FIG. 1E

COMPRESSED MEASUREMENT

OUTPUT SPECTRA

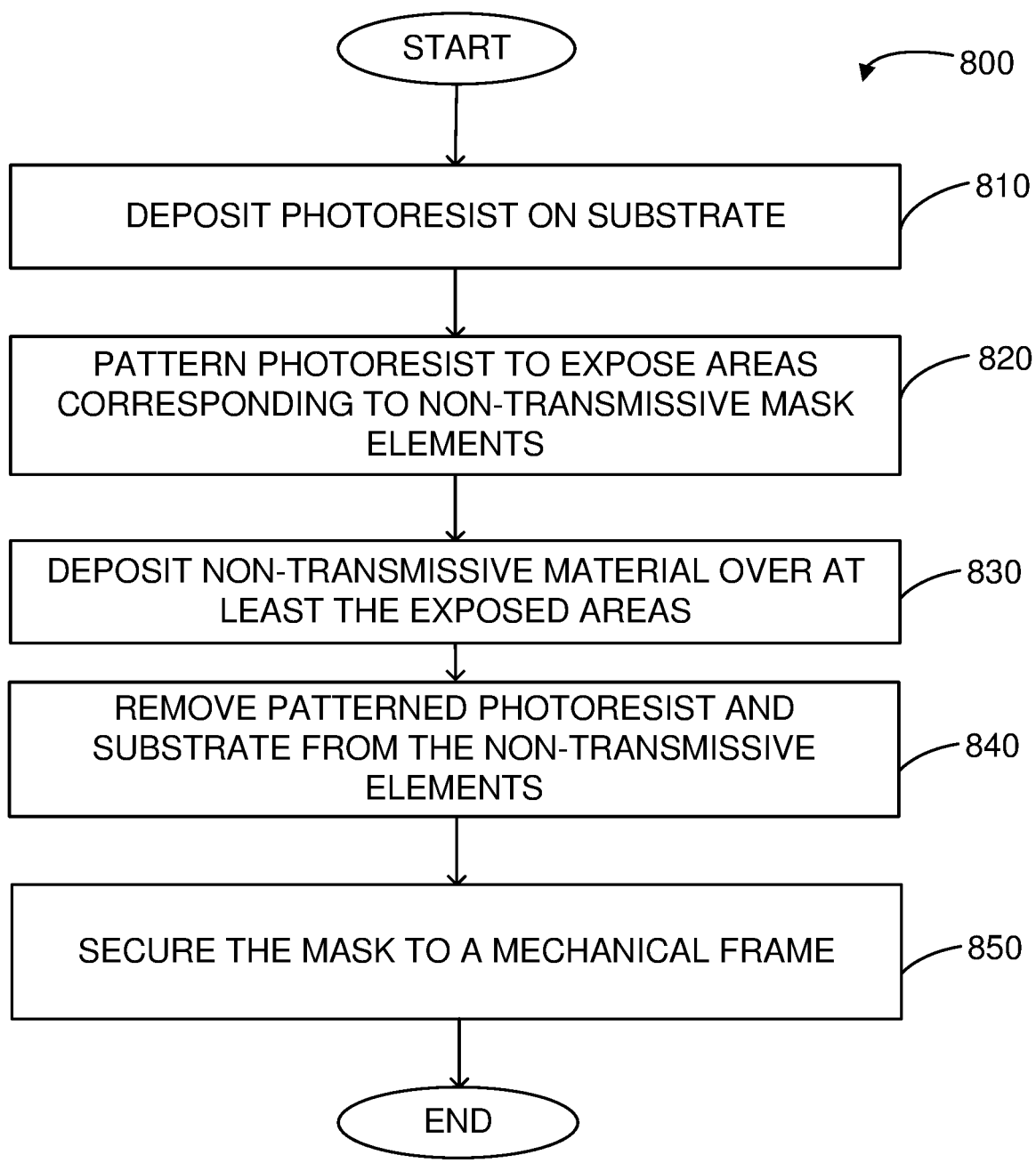

COMPRESSIVE SCANNING SPECTROSCOPY

CROSS REFERENCE TO RELATED APPCATIONS

This application claims the benefit of U.S. Provisional Application No. 62/330,004, filed Apr. 29, 2016, which is incorporated herein by reference in its entirety.

The disclosure of this application relates to compressive sensing as described in U.S. patent application Ser. No. 15/075,015, filed Mar. 18, 2016, and PCT Patent Application PCT/US2016/023286, filed Mar. 18, 2016, and U.S. Provisional Patent Application 62/134,932, filed Mar. 18, 2015, all of which are incorporated herein by reference.

ACKNOWLEDGMENT OF GOVERNMENT SUPPORT

This invention was made with government support under grants DE-FG02-03ER46057 and DE-AC05-76RL01830 awarded by the United States Department of Energy. The government has certain rights in the invention.

FIELD

The disclosure pertains to compressive sensing in electron microscopy.

BACKGROUND

The acquisition of spectral information for specimens has many practical applications. In many cases, acquiring this spectral information requires dividing a signal to be analyzed into a plurality of frequency ranges or "bins." This division often produces signal levels that have poor signal-to-noise ratio, so that data acquisition requires long integration times. This is particularly challenging for specimens that require point by point scanning for evaluation. For example, electron energy loss spectra (EELS) often exhibit poor signal-to-noise ratio, limiting the usefulness of EELS. Such problems can be even more difficult in hyperspectral imaging that seeks high resolution both spatially and spectrally. The use of high power electron beams and long exposure times could permit improved signal-to-noise ratio in electron microscopy, but such exposures tend to alter specimen characteristics. New approaches to obtaining spectral information are needed.

SUMMARY

Methods comprise combining coded spectra associated with a plurality of specimen locations, and, based on the combined spectra and associated encodings, determining spectra associated with each of the plurality of specimen locations. In some examples, the associated codings are based on modulations applied by a mask, and typically based on a mask pattern and a displacement of the mask. In some embodiments, each of the coded spectra is associated with a different coding and the coded spectra are combined on a sensor and obtained from the sensor. In representative examples, the coded spectra are obtained by, for each of the plurality of specimen locations, irradiating the specimen location with a probe beam, spectrally dispersing radiation received from the specimen in response to the irradiation, and coding the spectrally dispersed received radiation with a mask. In a representative embodiment, the coded spectra are electron energy loss spectra (EELS) and the irradiation is electron beam irradiation. According to additional examples, the mask includes a plurality of linear segments arranged so that each segment is associated with different electron energy and each of the linear segments is associated with a first electron transmittance or a second electron transmittance. In other examples, spectral data are summed at each specimen location so as to provide a specimen image.

Apparatus comprise a radiation beam scanner that selectively directs a scanned beam to a target area of a specimen. A mask is situated to receive spectrally dispersed radiation beams responsive to respective scanned beams and generate corresponding mask-modulated, spectrally dispersed radiation beams based on relative displacements of the mask and the spectrally dispersed radiation beams. A sensor is situated to receive the mask-modulated, spectrally dispersed radiation beams and produce an output signal corresponding to a sum of signals associated with the mask-modulated, dispersed radiation beams. According to some examples, the scanned beam is an electron beam. In further examples, an electron spectrometer is situated to receive electron beams responsive to the scanned beams, and produce corresponding spectrally dispersed radiation beams. In still additional examples, a displacement stage is coupled to the mask, and a scan controller is coupled to the displacement stage and the radiation beam scanner so as to select a stage displacement associated with a scanned target area. According to other representative examples, at least one displacement stage is coupled to the mask or the sensor, and a scan controller is coupled to the at least one displacement stage and the scan controller so as to select a stage displacement associated with a scanned target area. In a representative example, the displacement stage is piezoelectric stage. In still other examples, the sensor receives at least a predetermined set of the mask-modulated, spectrally dispersed radiation beams during a sensor frame time, and produces a compressed output corresponding to a sum of signals associated with the mask-modulated, spectrally dispersed radiation beams received during the frame time. According to some embodiments, the mask comprises a one-dimensional area of rectangular regions of a first transmittance interleaved with rectangular regions of a second transmittance that is different than the first. In typical examples, the sensor is situated to receive spectral components of the mask-modulated, spectrally dispersed radiation beams along sensor pixel rows and the rectangular regions of the mask are oriented in parallel to the sensor pixel rows.

Apparatus comprise an electron beam scanning system situated to sequentially scan a monochromatic electron beam over a selected set of specimen areas and produce corresponding electron beams having spectral components associated with energy loss. An electron spectrometer is situated to receive the electron beams having spectral components associated with energy loss and produce corresponding spectrally dispersed beams. An electron beam mask receives the spectrally dispersed beams with associated mask displacements and produces mask-modulated, spectrally dispersed beams based on the displaced mask patterns. An electron beam array sensor is situated to sequentially receive the mask-modulated, spectrally dispersed beams during a sensor frame time and produce a compressed output signal corresponding to a sum of signals associated with each of the mask-modulated spectrally dispersed beams. A processor is coupled to receive the compressed output signal and produce spectra for each of the specimen areas of the selected set based on the compressed output signal and the mask displacements.

The foregoing and other features, and advantages will become more apparent from the following detailed description, which proceeds with reference to the accompanying figures.

BRIEF DESCRIPTION OF THE DRAWINGS

FIG. 1C illustrates a sensor that includes a rectangular array of pixels.

FIGS. 1D-1E illustrate representative displacements of the mask of FIG. 1B with respect to an image sensor.

FIG. 8A illustrates an example method of generating a beam mask for compressive sensing.

DETAILED DESCRIPTION

Figure 1A:
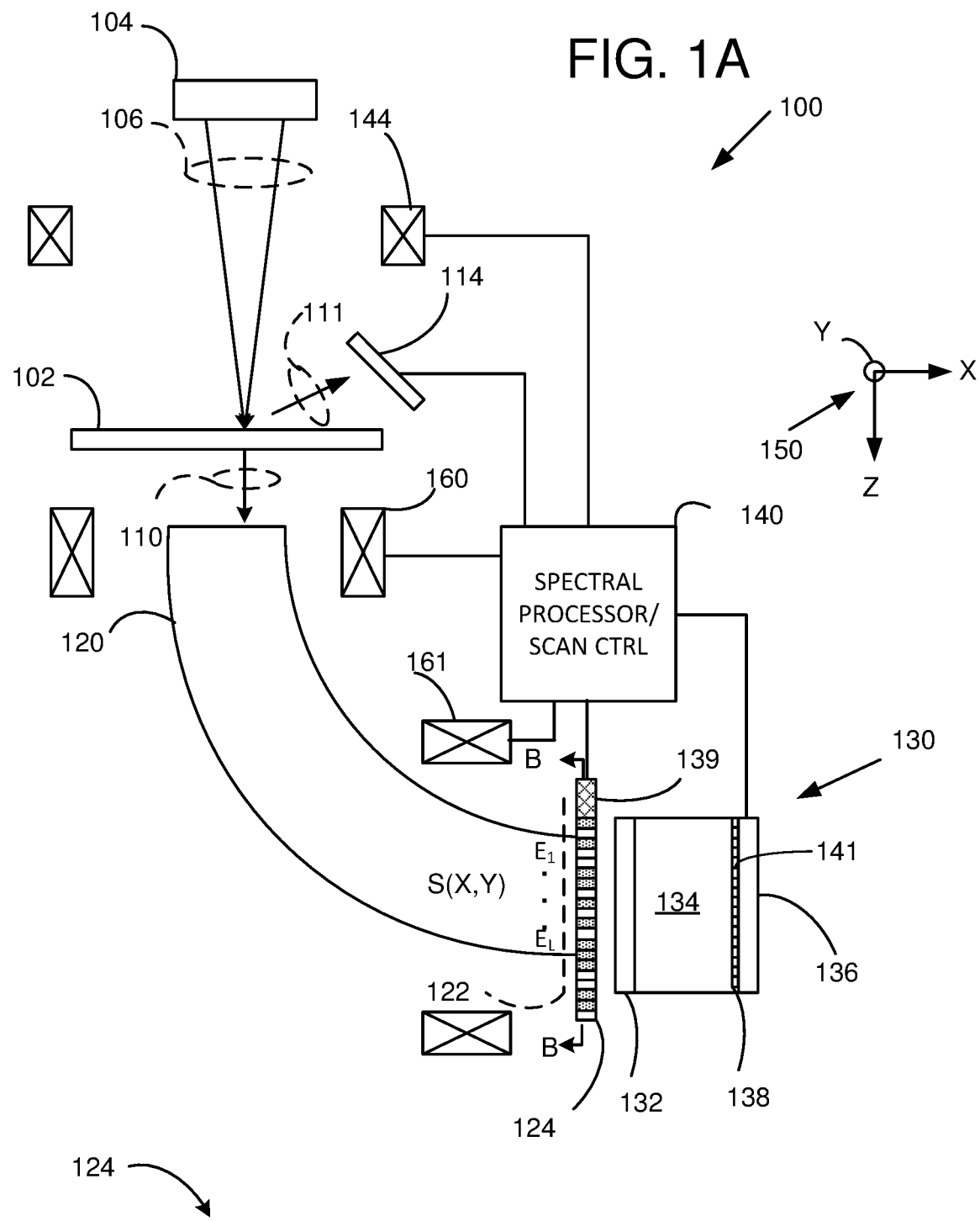
FIG. 1A illustrates an electron energy loss spectrum (EELS) system that includes a coded mask for compressive sensing.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and nonobvious features and aspects of the various disclosed embodiments, alone and in various combinations and subcombinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections. In some cases, examples are described with reference to directions indicated as "above," "below," "upper," "lower," and the like. These terms are used for convenient description, but do not imply any particular spatial orientation.

The disclosed methods and apparatus generally pertain to particle beam-based imaging systems and particle beam spectra, such as those associated with charged particles such as electrons or positively or negatively charged ions as well as spectra associated with electromagnetic radiation generally. As used herein, "radiation" or "radiation beam" refers to charged particle beams such as electron or ion beams, neutral particle beams such as neutron beams, electromagnetic radiation beams at wavelengths less than 400 nm such as extreme ultraviolet, soft X-rays, hard X-rays, and gamma ray wavelengths, visible wavelengths, or greater than infrared wavelengths such as far-infrared, microwave, millimeter wave, or longer wavelengths. Some radiation beams can be referred to as particle beams (e.g., ions, neutrons, electrons) while others can be referred to as high-energy electromagnetic radiation beams. Propagating electromagnetic radiation at wavelengths between 400 nm and 700 nm is referred to as a visible beam. Visible and infra-red beams can also be used. As used herein, the term "image" or "image beam" can refer to a spatial variation in a particle beam amplitude or phase, typically produced in a particle beam by a specimen under investigation. For example, in transmission electron microscopy (TEM), an image beam is produced by directing an electron beam to a specimen so that a transmitted beam has a spatially varying amplitude or phase associated with the specimen. In some examples, a charged particle beam (CPB) such as an electron beam is scanned across a specimen and spatial variations in the scanned beam correspond an image beam. In some disclosed examples, spectra associated with each or some locations in an image are acquired.

"Image" is also used to refer to a visible image such as obtained by displaying a CPB image on a display device or a fluorescent screen. In addition, the term image can also refer to a detected image corresponding to numerical values associated with spatial variations in CPB beam intensity or phase as a function of position. For example, image beams can be detected to produce an array of CPB intensity values I(x,y) that are a function of transverse coordinates (x, y). Such detected images can be recorded and stored in a computer-readable medium or transmitted as arrays, or in other image formats such as JPEG, TIFF, or other compressed or uncompressed formats. A sequence of beam images obtained at regular or irregular time intervals can be used to produce a corresponding sequence of recorded or stored images; such sequences are referred to as videos, video signals, or video sequences. A single image of a video sequence can also be referred to as a video frame. Images or spectra having modulations associated with compressive sensing (CS) can be referred to as compressed images/spectra or compressed video frames. In the disclosed examples, array detectors such as CCDs or direct detection cameras (DDCs) are typically used to detect spectrally dispersed particle beams or other beams. Such detectors generally integrate received particle beam intensity during a selectable frame duration. As used herein, an integration time is a time period in which a sensor array accumulates an image signal before capture and readout.

As used herein, the term "spectrum" can refer to a variation in a particle beam amplitude or phase that is a function of particle frequency or energy, typically produced in a particle beam by interaction with a specimen under investigation. For example, in transmission electron microscopy (TEM), a spectrally dispersed beam is produced by directing electrons from a specimen to a spectrometer. Spectrum can also refer to associated numerical values or stored numerical values. Spectrum refers generally to variations in radiation or radiation beam intensity, amplitude, phase, polarization, or other characteristic as a function of beam wavelength or beam particle energy.

In the disclosed examples, specimens are typically irradiated with a probe beam and radiation responsive to the probe beam is spectrally dispersed so that the amplitude, phase, power, power or other characteristic of interest is a function of position. Typically, spectral divergence is associated with different frequent components having a linear spread that is a function of wavelength or energy, but a linear energy or frequency spread not required. In one example, the probe beam is a monochromatic electron beam and a responsive beam is an electron beam having energies associated with electron energy loss in a specimen. Some of the examples below are described with reference to electron energy loss spectroscopy (EELS), but other spectral data can be acquired based on other probe beams and beams produced in response to a probe beam. In some examples, a probe beam is scanned with respect to a specimen to produce a secondary beam that is spectrally dispersed and then modulated for compressive sensing. In other examples, spectral components associated with plurality of specimen locations are obtained in or during a single beam exposure and modulated for compressive sensing.

In typical examples, particle beams or other radiation beams (generally after being spectrally dispersed) are modulated by transmission, reflection, scattering, or other interactions with one or more beam masks. Such a beam mask is generally divided into a plurality of mask elements arranged in an array, each of which can be arranged to produce a selected beam attenuation or phase change. In the examples disclosed herein, a mask that comprises a linear array of rectangular segments is convenient, as each rectangular segment can be situated to receive responsive radiation over a selected spectral range (spectral bin). Typically, the mask elements are arranged as a first set of mask elements and a second set of mask elements, wherein the first and second sets of mask elements produce first and second attenuations and/or phase changes or other modulations, respectively, wherein the first and second attenuations and/or phase changes are different. Mask elements can have varying dimensions and aspect ratios. For convenient description, mask areas are referred as transmissive or non-transmissive. As used herein, non-transmissive refers to transmittances of less than 25%, 10%, 5%, 1%, or 0.1%; transmissive refers to transmittances greater than 5%, 10%, 25%, or 50%. Typically values are selected so that a ratio of transmittances is at least 5:1, 10:1, 20:1, or 100:1. As used herein, a reference or "standard" attenuation for a radiation beam at a selected wavelength or of a selected particle type is an attenuation that corresponds to 300 kV electron beam blocking provided by a 25 µm thickness of gold.

In some cases, beam masks having first and second pattern areas with an attenuation difference that is about the same as the reference attenuation are suitable. A particle beam that has been acted upon by such as mask can be referred to as a mask-modulated particle beam. Modulation for compressive sensing (CS) can be applied to particle beams with masks or in other ways, and such particle beams generally referred to as modulated or encoded beams. For some types of radiation, spatial light modulators (SLMs) are available that permit modulating radiation beams by varying characteristics of the SLM. Liquid crystal based SLMs can be used for some wavelength ranges.

The term "signal" as used herein generally refers to a time-varying particle beam intensity or phase, or a time-varying electrical current or voltage, and such signals are typically processed as a sequence of electrical images represented as image currents or voltages.

In the disclosed examples, beam masks are situated at particular locations for convenient illustration. For examples in which a beam mask is situated at plane associated with a sample spectrum, such a beam mask can generally be situated at other locations that are optically conjugate to the specimen. Conjugate planes can be provided with one or more beam lenses that image such planes onto each other via one or more intermediate planes.

In the disclosed examples, binary masks are used in which some mask pattern areas apply a first modulation and other mask pattern areas apply a second modulation. These modulations are conveniently described as amplitude modulations but other types of modulations can be applied. In addition, masks having two, three, or more sets of pattern areas that apply respective modulations can be used. For example, three sets of pattern areas can apply first, second, and third modulations respectively. CS-based systems can use such modulations as well. Such masks can use different thicknesses or types of material or combinations thereof to provide such different modulations. These differing modulations can be between 0% and 100% for masks that provide amplitude modulation. However, for convenient illustration, the examples are described with reference to binary masks.

The disclosed examples use image sensors or direct charged particle sensors that include two dimensional arrays of individual sensor elements but one dimensional (linear arrays) are suitable, and single individual detectors can also be used. With single detector, masking of spectral bins is not used, and a detector is placed at locations associated with the spectral bin to be acquired.

Introduction

Compression of a signal can reduce an amount of data needed to represent or acquire spectral information about a specimen, while maintaining or improving signal to noise ratio, or provide other signal analysis and acquisition features, typically based on the use of signal sparsity and incoherence. Compression can occur after videos, images, diffraction patterns, spectra or other data have been captured and stored. However, as described herein, compression can occur during data acquisition. Compressive sensing combines sensing and compression in one operation to increase the resolution or speed of any detector (both CCDs and DDCs). Using CS, fewer total measurements may be required, which, when applied to particle beam data capture, can potentially increase the acquisition speed, reduce required particle beam dose, and/or increase signal-to-noise ratio.

As one example, modulation is applied by directing a spectrally dispersed particle beam received from a sample to a particle beam mask and then to an image sensor. The mask can be moved at a fixed or variable rate or stepped so that a sequence of spectral data for a set of specimen locations associated with different modulations or encodings by the mask is acquired and combined in a single frame. Alternatively, a modulation can be applied to a dispersed particle beam with a stationary mask, and the dispersed particle beam scanned over the mask. Upon acquisition of a sequence of modulated spectra, the spectra can be decompressed as described below. In one example, a sequence of encoded EELS is acquired, and a reconstructed (i.e., decompressed) sequence can be obtained so that energy loss throughout a specimen is obtained. Using CS, specimen spectra can be compressed at the time of measurement and accurately recovered at a later time with suitable decompression using hardware and/or software. In some respects, the CS methods and apparatus disclosed herein are counterintuitive to traditional signal acquisition techniques which sample and then compress the sampled data.

Compressed measurements for CS-EELS can be obtained by spatially and/or temporally modulating a spectrally dispersed EELs beam with a coded aperture mask. For example, a spectrally dispersed beam can be directed to a coded aperture mask that applies a modulation to the beam at a rate faster than a rate at which an image sensor produces images. Such a modulation can provide compressed spectra based on multiple mask encodings associated with corresponding specimen locations. Modulation can be applied in various ways. As one example, a mask is translated or otherwise subjected to a time-varying displacement using one or more translation stages, such as piezoelectric stages as a probe beam is scanned to different specimen locations. Such stages can be moved along one or more axes based on applied stage drive signal. If a triangular wave drive signal having up and down ramp portions is used, sets of encoded spectral data can be obtained during the up ramp and the down ramp. Different positions of the mask with respect to the spectrally dispersed beam establish different encodings, and different masks are not required to produce different encodings. Since a time-varying position of the mask can be obtained based on the applied stage drive signal, encoding as a function of time is known. A compression ratio can be determined based on a range of motion of the mask. Effectively, moving n feature sizes or pixels of the mask can provide a compression ratio of n and n differently encoded spectra are combined in single frame captured by an image sensor if a suitable image integration time is selected. To produce a CS modulated spectrum, these n different images are to be integrated into a single frame. The CS modulated spectrum is then processed or "decompressed" to extract individual spectra.

As described herein, particle beam imaging systems using CS include a mask such as a self-supported, single-piece mask that includes a plurality of mask regions that apply different modulations. For example, the mask regions can selectively apply different amplitude or phase modulations. In convenient examples, such a mask for particle beam imaging using transmission includes mask regions that are substantially non-transmissive and mask regions that are substantially transmissive. Such a mask can be formed by patterning transmissive and non-transmissive regions on a substrate, and an array of patterned regions removed from the substrate. For example, non-transmissive regions can be formed using electroplating of materials that are non-magnetic and have a high blocking power for charged particles, such materials having large atomic numbers. The transmissive regions can be voids or holes in the non-transmissive regions. Generally, any patterned arrangement of regions with differing attenuations can be used for transmission particle beam imaging. Typically, a linear array of mask features situated along an axis associated with spectral dispersal is suitable.

Example 1

With reference to FIGS. 1A-1E, a system 100 for acquiring electron energy loss spectra for a specimen 102 includes an electron beam source 104 that provides a suitably monochromatic electron beam 106 that is directed to a selected specimen area. For convenient description, specimen areas are identified with coordinates X, Y of a right-handed coordinate system 150 in which a Y-axis is perpendicular to the plane of FIG. 1A. Specimen locations can also be identified with coordinates I, J, wherein I, J are integers that refer to stepwise displacements of scanned areas. A spectrum associated with a particular specimen area can be referred to as S(X,Y) or S(I,J).

Interaction of the electron beam 106 and the specimen area produces a secondary electron beam 110 and typically an X-ray beam or other beams that can be directed away from the specimen 102 on either side of the specimen 102. In a typical example, the secondary electron beam 110 is transmitted by the specimen 102 and has an energy spectrum that can be used to characterize the irradiated specimen area. Other possible beams can be detected by a detector 114 such as X-ray beams or elastically or inelastically backscattered electron beams shown schematically as a beam 111.

The secondary beam 110 is directed to an electron spectrometer 120 that disperses the secondary beam as a function of electron energy so that at spectrometer output 122, electron energy is a function of position. A mask 124 is situated to modulate the spectrally dispersed electron beam by selectively transmitting or blocking electrons of certain energies, and the modulated beam is coupled to an electron detector 130. The electron detector 130 includes a scintillator layer 132 optically coupled to a fiber-optic bundle 134 that is coupled to a charge-coupled device (CCD) image sensor 136. The CCD 136 includes an imaging array 138 of light sensors 141 (also referred to herein as pixels) that are arranged in rows that extend in a direction parallel to the Y-axis and columns that extend in a direction parallel to the Z-axis. The imaging sensor 138 is controlled so as to accumulate charge associated with a received scintillation light signal during a frame time; at the end of a frame time, the accumulated charge is readout as an image signal and the light sensors 141 are reset prior to acquisition of a subsequent signal.

The mask 124 is coupled to a piezoelectric translator or other displacement device 139 that is coupled to and controlled by a controller 140 that provides suitable voltages and or currents for producing suitable mask displacements along one or two axes, though typically a single axis displacement is suitable. The controller 140 is also coupled to the detector 114, situated in FIG. 1A to detect an X-ray beam or a scattered electron beam. A mask such as the mask 124 can also be provided for this detector but is not shown in FIG. 1A. The controller 140 is also coupled to a beam scanner 144 such as electrostatic deflection plates or scanning coils.

Figure 1B:
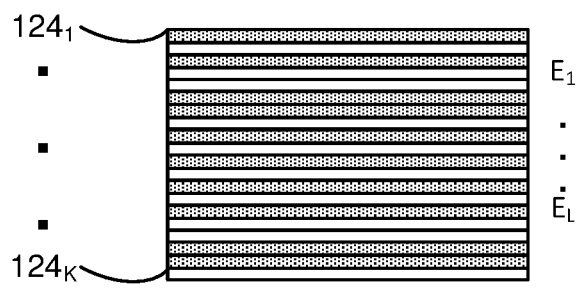
FIG. 1B illustrates a representative mask for used in the system of FIG. 1A.

Spectral data (EELS data, for example) for the specimen is obtained by scanning the beam over selected portions of the specimen and accumulating spectral data with the detector 130 for some but not all spectral bins. As shown in FIGS. 1A-1B, the spectrally dispersed beam is incident to the mask that includes a plurality of pattern areas $124_1, \ldots, 124_K$ situated to block or transmit selected portions of the EELS spectrum. Transmissive areas are shown without shading; beam blocking or attenuating areas are shown with shading. Pattern area transmittance for each pattern area can be randomly selected and typically about 50% of the spectral data is blocked by the mask 124. The pattern areas $124_1, \ldots, 124_K$ can be conveniently arranged as rectangular areas having a length in a Y-direction that is adequate to capture substantially all of the spectrally dispersed beam and a width in a Z-direction that is an integer multiple of a pixel width in the Z-direction. With such rectangular mask areas, portions of the spectrally dispersed data associated with some or all spectral bands produce scintillation light that is captured by a corresponding row or rows of pixels 141. Signals associated with all pixels in the row or rows associated with some or all spectral bands can be summed. For purposes of illustration, a representative arrangement of spectral bands (electron energies $E_1, \ldots, E_L$) is shown as situated with respect to the mask 124 in a particular arrangement.

Alternatively, spectrally dispersed beam or beams can be scanned or translated with respect to a fixed mask. For example, beam deflectors such as beam deflectors 160, 161 can be situated to produce beam deflections with respect the spectrometer 120. Electrostatic, magnetic, or other beam deflectors can be used as convenient. For some types of radiation beams, beam deflection can be more difficult, and mask displacements can be more readily implemented. A combination of spectral beam displacement and mask displacement can be used, as preferred. For convenience, a beam deflector situated to produce a displacement of a spectrally dispersed beam can be referred to as a spectral beam scanner or spectral beam deflector.

For radiation such as visible light, a spatial light modulator (SLM) can be used to define mask patterns that are varied to produce modulations similar to those produced with a mask. In some cases, SLMs can require use of polarizers to provide modulation.

It is generally convenient to fix the location of the detector 130 and positions of spectral bands at the spectrometer output 122. Then, as shown in FIGS. 1D-1E, the displacement device 139 can be used to displace the mask 124 along the Z-axis with respect to the imaging array 138. For each displacement, different selections of spectral ranges are blocked or attenuated. The controller 140 and the imaging array 138 can be arranged to sum signals associated with each row for a single position of the mask 124. However, generally different portions of the specimen 102 are irradiated and the mask 124 set so as to have an associated mask displacement for each specimen portion during a single image sensor frame time. In this way, spectral data for different spectral ranges and different image portions are accumulated by the imaging sensor 138 in a single frame time. Representative relative displacements of the mask 124 and the image sensor 138 are shown in FIGS. 1D-1E. Similar modulations of spectrally dispersed beams can be produced by scanning the spectrally dispersed beam or beams with a fixed mask. In this case, sensor rows are situated to receive radiation beam portions associated with different spectral bands as a function of spectral beam scanning. In either case, the compressed spectra can be decompressed to recover or extract individual spectra.

Example 2

Figures 2, 3:
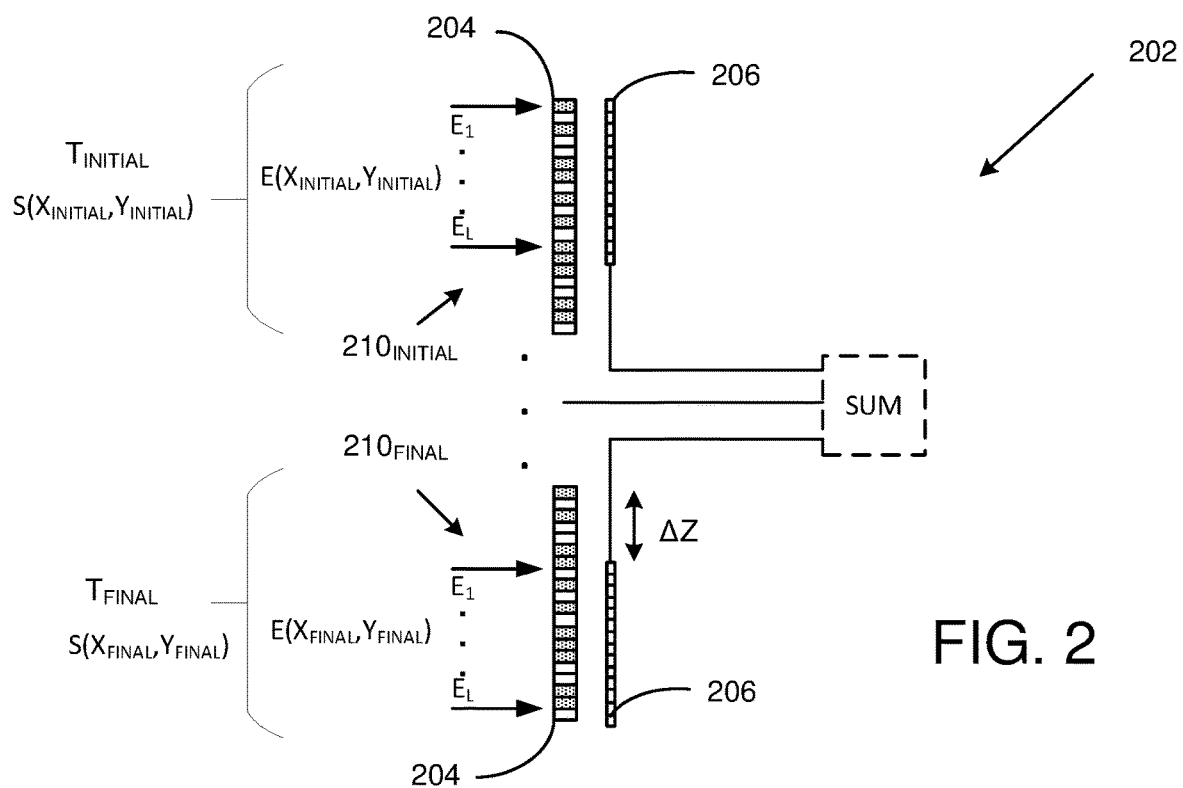
FIG. 2 illustrates combining signals associated with coded, spectrally dispersed beams during a single sensor frame time.
FIG. 3 illustrates compressed spectral data acquisition.

An example of compressed spectral data acquisition is illustrated with reference to FIG. 2. Spectrally dispersed beams $210_{INITIAL}, \ldots, 210_{FINAL}$ associated with specimen locations $(X_{INITIAL}, Y_{INITIAL}), \ldots, (X_{FINAL}, Y_{FINAL})$, respectively, are incident in sequence to a mask 204 during a sensor integration time or frame time. The mask 204 selectively transmits or blocks spectral ranges, and the exposure for each specimen location is associated with a corresponding mask displacement $\Delta Z_{INITIAL}, \ldots, \Delta Z_{FINAL}$. The transmitted (mask-modulated) spectrally dispersed beams produce scintillation light associated with a plurality of transmitted ranges, and the scintillation light associated with each transmitted spectral range is coupled to an image sensor 206. Specimen locations $(X_{INITIAL}, Y_{INITIAL}), \ldots (X_{FINAL}, Y_{FINAL})$ are irradiated during a single frame time of the image sensor 206 so that the modulated spectra are effectively summed by the image sensor 206. In the example of FIG. 2, the image sensor 206 is fixed with respect to the spectral distribution produced by a spectrometer, but the mask 204 is displaced for each acquisition, i.e., for each spatial location of the series. In other examples, one or both are moved to obtain a selected displacement. Typically, each row of pixels of the image sensor 206 acquires EELS data for a common spectral band but for a plurality of specimen locations.

Example 3

Compressed spectral data acquisition is further illustrated in FIG. 3. In FIG. 3, $H_I$ is a mask function corresponding to the arrangement of transmissive and non-transmissive areas of the mask and a relative position of the mask for an $I^{th}$ specimen location; $S_I$ is a spectrum associated with the $I^{th}$ specimen location. For EELS, $S_1$ is signal as a function of electron energy. A compressed signal Y is obtained as a sum of the products of a mask function and a spectrum for each selected specimen location. As shown the compressed spectrum Y is a function of mask-modulated spectral values from multiple locations.

Example 4

Figure 4A:
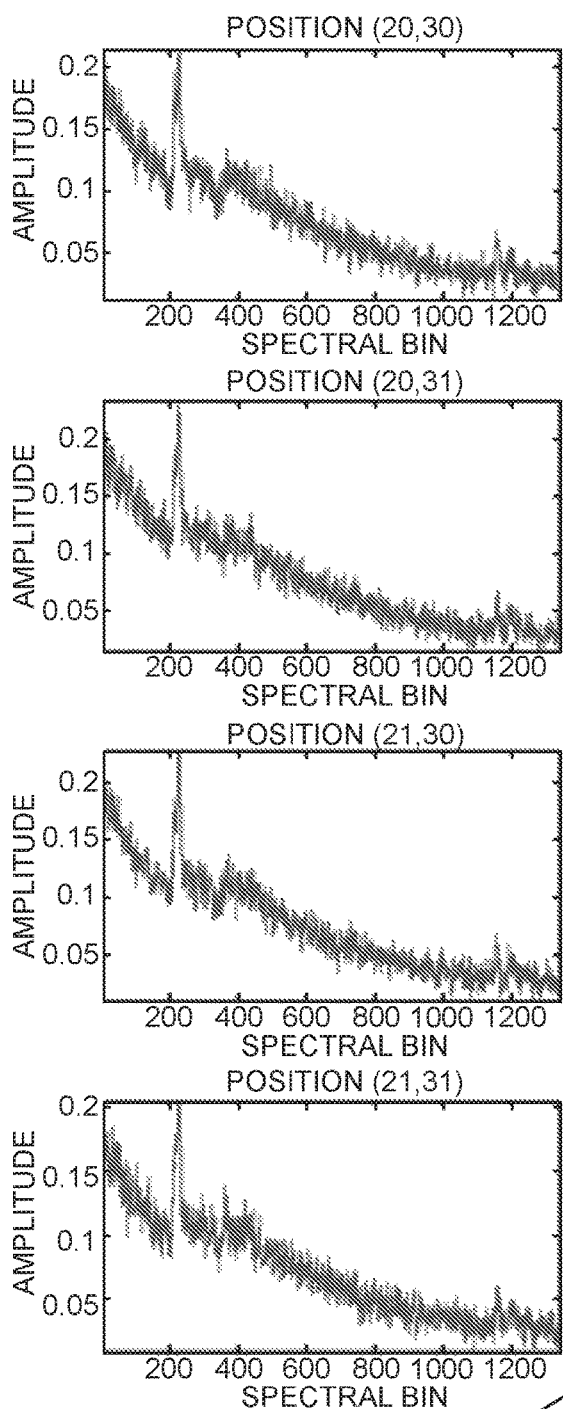
FIG. 4A illustrates spectra associated with four specimen locations obtained using a JEOL ARM200 scanning transmission electron microscope (STEM). The specimen is a Pr-doped STO Σ13 grain boundary sample.
Figure 4B:
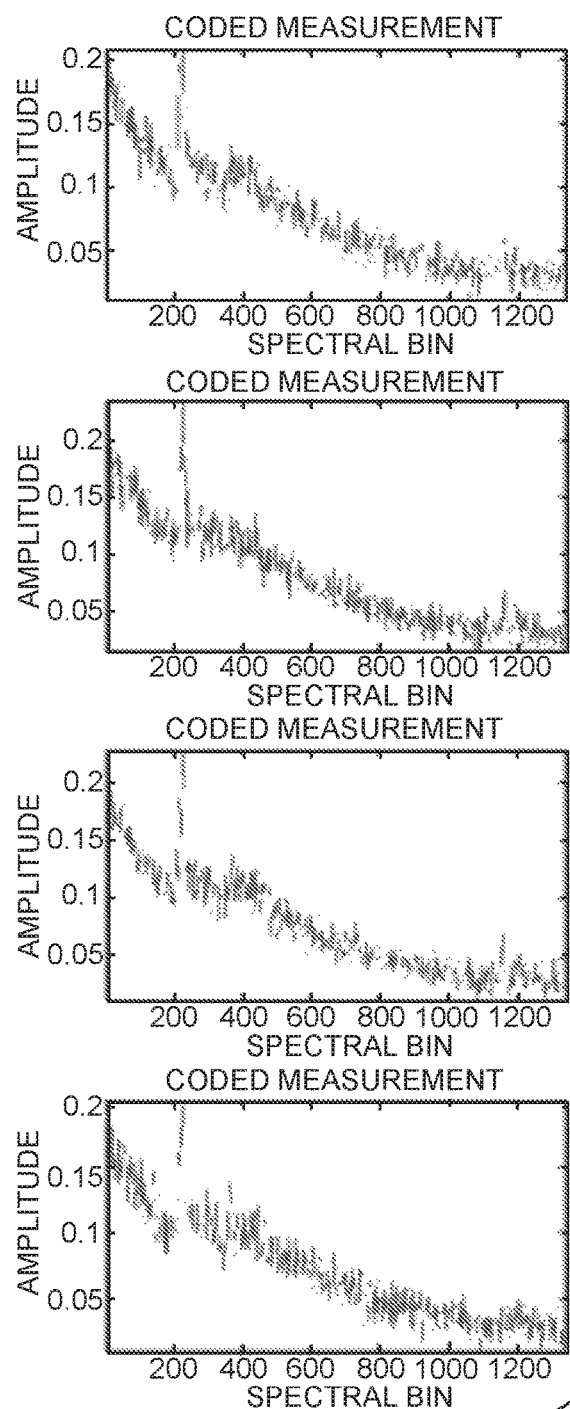
FIG. 4B illustrates coded spectra corresponding to the spectra of FIG. 4A.
Figure 4C:
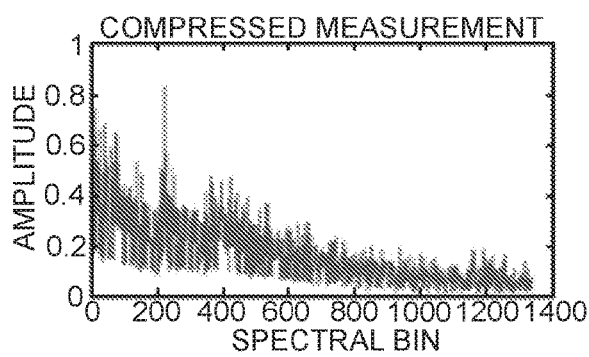
FIG. 4C illustrates a compressed signal.
Figure 4D:
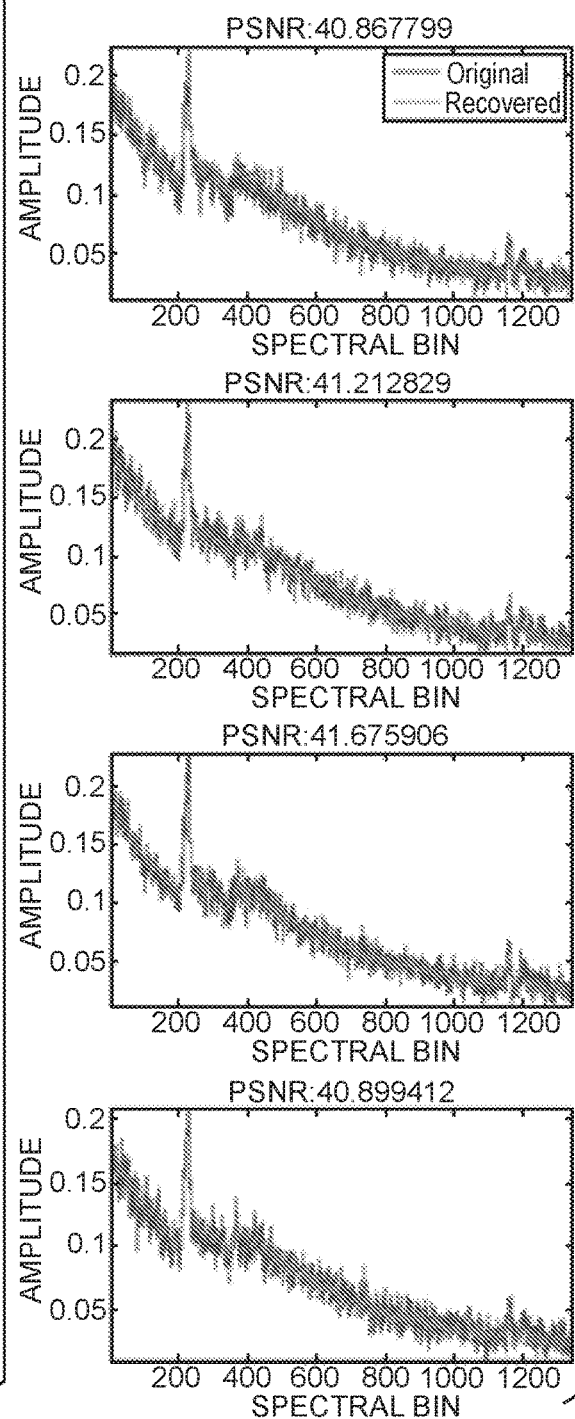
FIG. 4D illustrates decoded spectra and spectra obtained without encoding showing improved signal-to-noise ratio available with coding.

Representative model spectra (uncoded, i.e., without modulation by a mask) are shown in FIG. 4A for specimen portions at four specimen locations at relative coordinates (20,30), (21,30), (20,31), and (21,31). The spectra of FIG. 4A are obtained by direct measurement, without compression. FIG. 4B shows corresponding coded (i.e., with modulation by a mask) spectra. These spectra correspond to data that typically is integrated at a sensor so that the data of FIG. 4B is not generally recorded. FIG. 4C illustrates the summation of the coded measurements of FIG. 4B to produce a compressed signal. This signal is a function of electron energy, but contains contributions from all four selected specimen locations. FIG. 4D illustrates spectra associated with each specimen location after decompression (decoding) of the compressed signal, exhibiting improved signal-to-noise ratio.

A block of specimen locations such as used in FIGS. 4A-4D is convenient as a probe beam need be scanned only to an adjacent specimen location. However, any set of specimen locations can be used arranged along one or more lines, in a rectangular block, as a randomly selected set, or in other ways. Non-adjacent locations may be preferred as such locations generally tend to have uncorrelated properties. However, beam scanning to adjacent locations is typically simpler to implement.

Example 5

Figure 5:
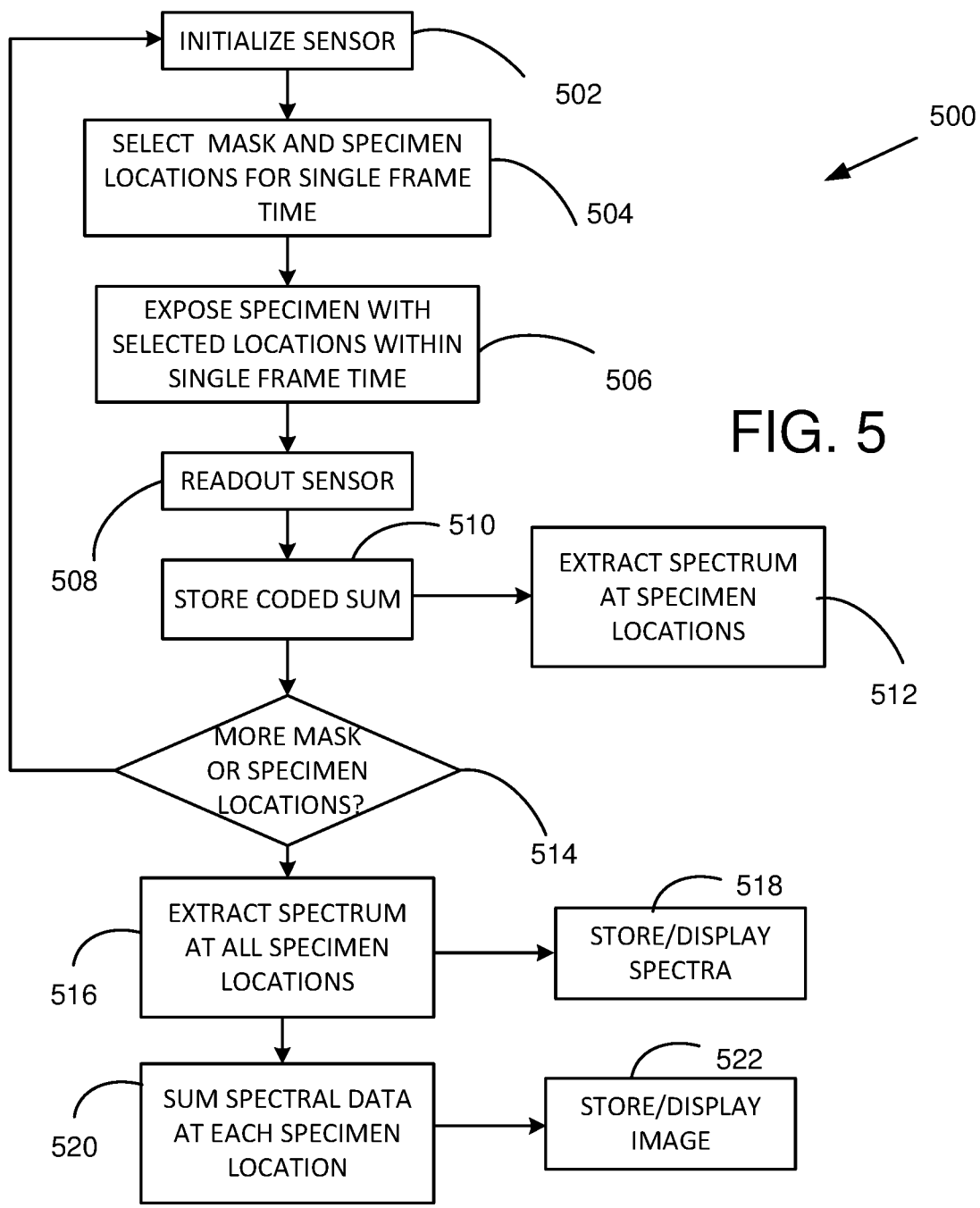
FIG. 5 illustrates a representative method of obtaining and decompressing compressed data associated with coded, spectrally dispersed data received from a sensor.

Referring to FIG. 5, a representative method 500 includes initializing a sensor at 502, typically by resetting any previously acquired data. For a CCD sensor, accumulated charge is discharged. A frame rate or frame time can be selected that determines a time available for acquiring coded spectra to be summed by a detector. At 504, specimen locations for measurement along with corresponding mask displacements are selected. A number of locations can be limited by the frame time as well as the need to acquire sufficient signal for each location. At 506, the selected specimen areas are irradiated in series and corresponding mask displacements made until all selected specimen areas have been exposed. At 508, the coded sum measurement is read-out and stored at 510; if desired, the coded measurement can be uncompressed at 512. At 514, additional specimen areas can be selected and processing returns to 502. Otherwise, all compressed measurements can be uncompressed at 516 and stored or displayed at 518 so that EELS are available for the specimen. If desired, spectral data can be summed at each location to obtain a specimen image at 520 that can be displayed or stored at 522.

Example 6

Figure 6:
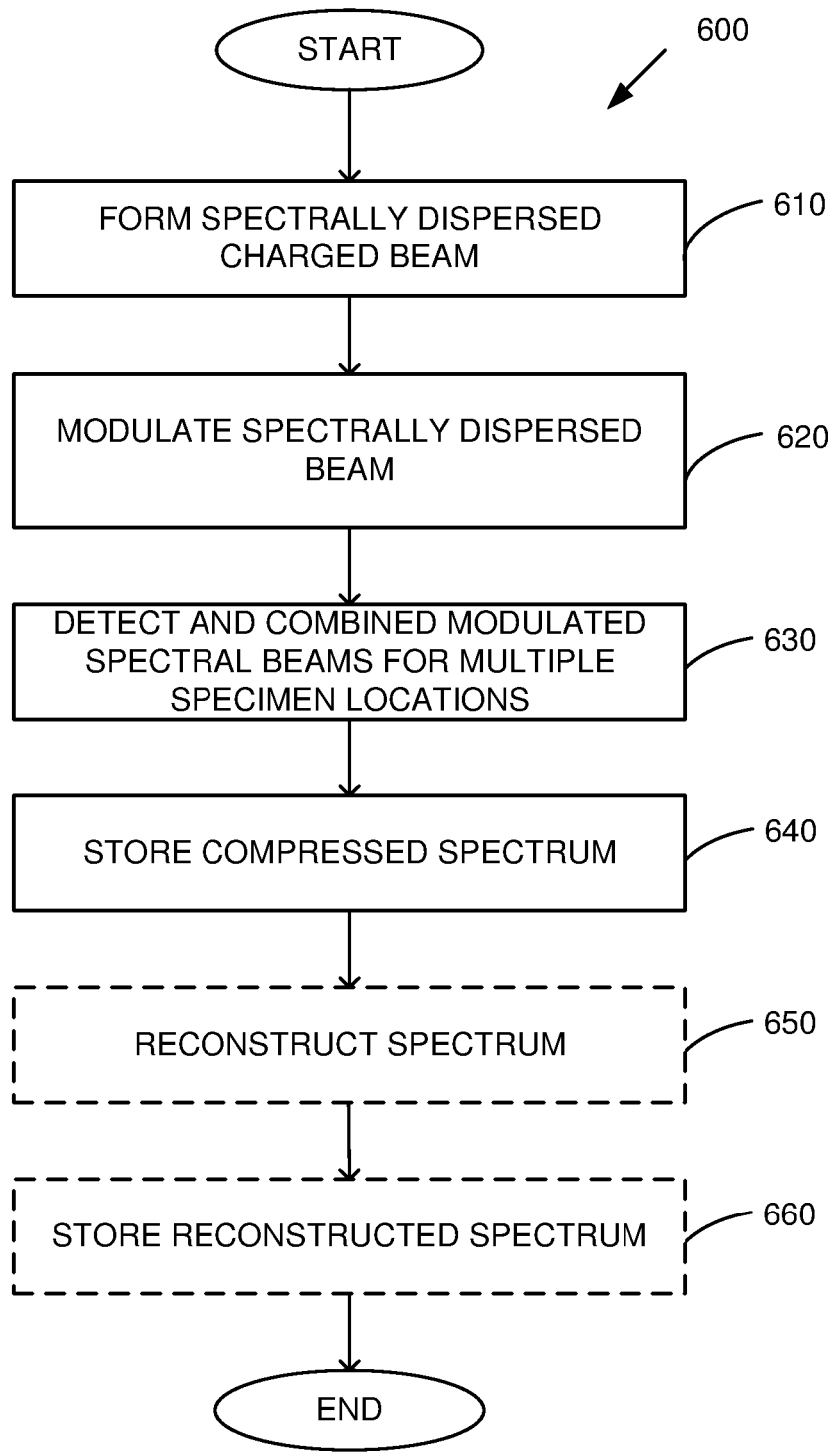
FIG. 6 illustrates another representative method of obtaining and decompressing compressed data associated with coded, spectrally dispersed data received from a sensor.

FIG. 6 illustrates an example method 600 for CPB spectral analysis using CS. Such a method can be implemented using various CPB imaging systems. At 610, a spectrally dispersed charged particle (CP) beam is formed by, for example, exposing a sample to a CPB such as an electron or ion beam and directing a beam from the sample to a spectrometer to produce a spectrally dispersed beam. At 620, the spectrally dispersed beam can be spatiotemporally modulated using a displacement of the beam with respect to a mask. The beam modulation is typically based on position of a mask that can be determined in a variety of ways including by moving a mask with respect to the beam and/or by moving or scanning the beam relative to the aperture. As one example, the beam is modulated by mechanically moving the mask using a translation or positioning stage.

At 630, modulated, spectrally dispersed beams associated with a set or block of specimen locations are detected using a sensor array that detects a varying intensity of the modulated beam. The modulated beam scan cover all of or a portion of a sensor array area. For example, the modulated beam can be directly sensed by CMOS sensors of a DDC or indirectly sensed using a scintillator and a CCD array. Spectrally dispersed beams associated with a plurality of specimen locations can be collected and summed by a sensor during a sensor integration or exposure time.

At 640, the detected compressed spectral data can be stored in a computer readable medium. The compressed spectral data can be stored in association with metadata such as a timestamp, sequence number, or other information about relationships to other spectral data or to specimen location or mask location. In some examples, a timestamp can be used to determine mask position (and hence, mask modulation) for decoding. The computer readable medium can include one or more of volatile memory, non-volatile memory, removable medium, non-removable medium, and/or any other medium which can be used to store information in a non-transitory way and which can be accessed by a processor of the imaging system.

At 650, uncompressed spectral data is reconstructed from the compressed data using compressive sensing reconstruction. For example, a processor can execute a software reconstruction module that uses one or more compressed spectra stored on the computer readable memory to create the uncompressed frame. At 660, the uncompressed spectral data is stored in a computer readable medium.

An integration or frame-grab of a spectrally modulated image beam with a sensor array can be synchronized with the movement a scanned beam that irradiates the specimen. The encoded mask can be moved in a predetermined pattern in one or more directions, but as spectra are generally dispersed along s single axis, movement in a linear direction along a single axis is typically sufficient. The amount and velocity of movement caused by the positioning stage can be controlled based on various factors, such as a maximum range of the positioning stage.

Example 7. Image Acquisition and System Control

Figure 7:
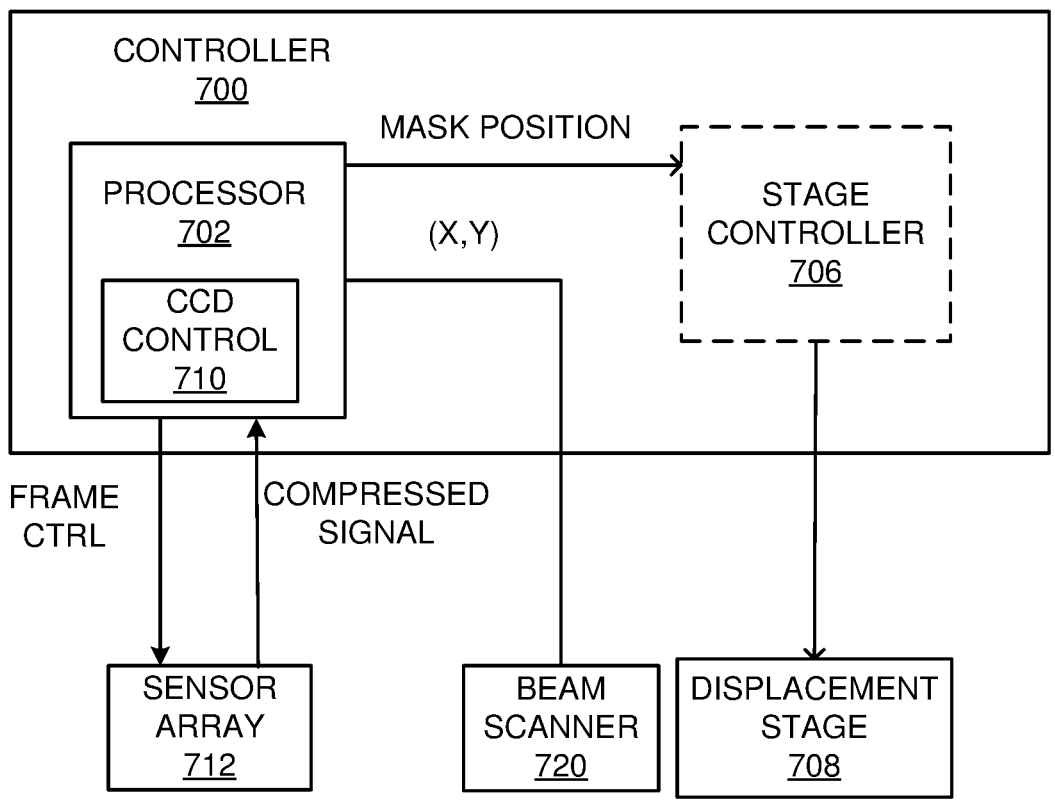
FIG. 7 illustrates an example controller for controlling a movable mask.

FIG. 7 illustrates an example controller 700 which can be implemented using a desktop, laptop, tablet, handheld or other computer system for controlling mask displacement and specimen irradiation. The controller 700 includes a processor 702 that is coupled to one or more displacement stages 708 so as control or receive a mask position. The processor 702 is coupled to a sensor controller 710 such as a CCD controller that is coupled to a sensor array 712. The processor 702 initiates data acquisition by the sensor array 712 and receives, stores, and processes spectral data, typically compressed spectral data, received from the sensor array 712. The sensor array 712 is coupled to receive a frame control signal that determines sensor integration time. In some cases, frame control is provided at the sensor array 712, and need not be supplied from the processor 702. The processor 702 initiates spectral data acquisition and generates stage control signals which in some cases, require additional processing such as amplification. The processor 702 can execute computer-executable instructions to communicate with and initiate and terminate actions of a beam scanner 720, the sensor array 712, and the stage controller 706 so that beam scanning, mask displacement, and sensor array frames are suitably sequenced.

Example 8. Mask Fabrication

FIG. 8A illustrates an example method 800 of generating a mask for a charged particle beam system using compressive sensing. At 810, photoresist can be deposited over an area of a substrate. The substrate can be used as support structure for the aperture mask during manufacture of the aperture mask. The substrate can be glass or silicon, for example. In one embodiment, the substrate can be conductive or can include a monoatomic or thicker layer of a conducting material on a substrate surface. A photoresist can be selected based on a variety of factors, such as a resolution or sensitivity of the photoresist, for example. The photoresist can be applied in various ways to produce a uniform thickness that is typically at least as thick as a CPB attenuating material to be deposited. In some examples, photoresist layers of thickness greater than 30 µm or greater than 100 µm are formed. A photoresist layer can be formed by spin coating, spray coating, or roller coating onto a substrate surface. The photoresist layer can be cured by air drying and/or by curing at a temperature exceeding room temperature, for example.

At 820, the photoresist is patterned to uncover or expose areas of the substrate corresponding to mask elements that are intended to be attenuating or non-transmissive to a CPB. In particular, the patterned photoresist layer can define photoresist areas corresponding to rectangular transmissive elements of a CPB mask and areas of exposed substrate corresponding to non-transmissive elements. A photoresist layer can be patterned by exposure to a positive or negative image of an intended mask pattern so as to selectively expose areas of the photoresist. The photoresist material can be a positive or negative photoresist which exhibits increased or decreased solubility after exposure. The photoresist is developed using a solvent or etchant that removes exposed or un-exposed areas, depending on whether a positive or negative photoresist is used. If a positive photoresist layer is used, photoresist areas corresponding to non-transmissive mask areas are removed by developing. Alternatively, if a negative photoresist layer is used, photoresist areas corresponding to the transmissive mask elements are exposed, and the photoresist at non-transmissive areas of the mask can removed.

At 830, a non-transmissive material is deposited over at least the exposed substrate areas. The non-transmissive material is deposited using electroplating, sputtering, evaporation, or other process to a thickness sufficient to produce a selected CPB attenuation. At 840, the patterned photoresist layer is removed along with any non-transmissive material deposited on the photoresist layer, and the substrate is removed from at least areas associated with mask elements that are to be transmissive. At 850, the mask is secured to a mechanical frame with glue, soldering, or other process. In some examples, a portion of the substrate to which photoresist is applied can be retained to serve as a frame.

Using electroplating for depositing a non-transmissive material may permit mask elements to have straighter, sharper edges. Such edges may improve image quality in a mask-modulated image by reducing reflections from sides of non-transmissive mask elements. In an alternative method, a material (such as a metal) is deposited at a desired thickness on a substrate and the resulting metal layer lithographically processed to remove the material at areas associated with transmissive mask elements. For example, a photoresist can be applied to a metal layer formed on a substrate. The photoresist layer can be patterned and exposed so that portions of the metal layer and the substrate associated with non-transmissive mask elements are exposed and can be etched to remove or thin. In some examples, such etching can create conical holes due to isotropic etching of the substrate that can result in reduced image quality due to reflections from the sides of the aperture mask.

Figure 8B:
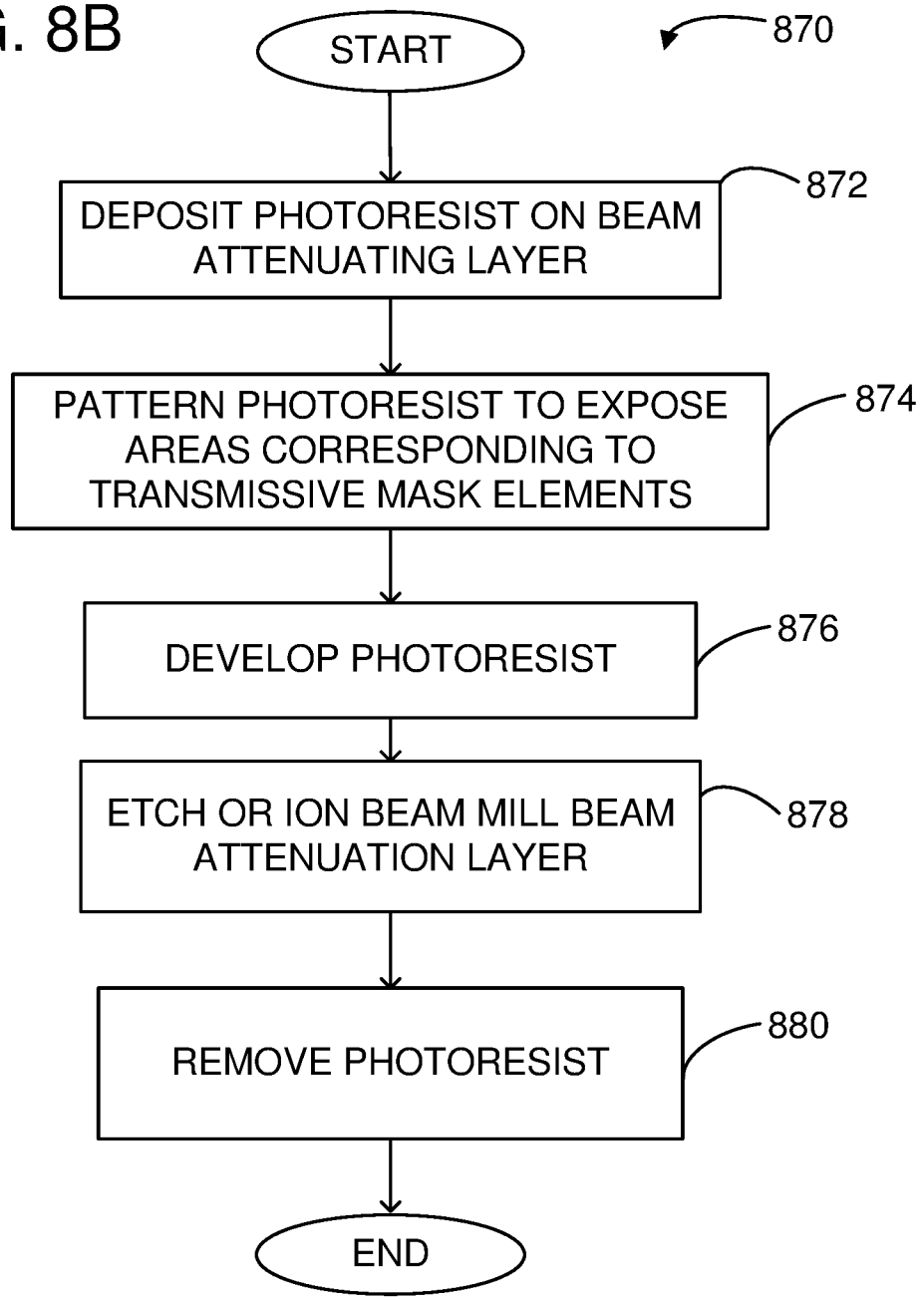
FIG. 8B illustrates another example method of generating a beam mask for compressive sensing.

Another method 870 of fabricating a radiation beam mask is illustrated in FIG. 8B. At 872, a photoresist layer is deposited on a beam attenuation layer, such as a gold layer that can be provided as a foil layer. For convenient processing, such beam attenuation layer can be secured to another substrate for simpler handling during processing. At 874, the photoresist layer is exposed to a mask pattern, and at 876, the photoresist is developed 876 so that portions of photoresist remain at mask areas that are to be relatively more attenuating while at areas that are to be relatively less attenuating, the beam attenuation layer is exposed. The exposed areas of the beam attenuation layer are wet etched, dry etched, or ion beam milled at 878 to reduce beam attenuation layer thickness, and in some examples, holes in the beam attenuation layer are formed. In some cases, direct etch or milling processes are preferred. At 880, the photoresist layer is removed, and the patterned beam attenuation layer can be secured to a frame.

In other alternatives, a beam attenuating layer is directly machined by ion beam milling or other process without a photoresist protective layer. In some examples, a beam attenuation layer on a substrate is processed to define mask areas having different attenuations. The substrate is selected to be substantially transparent to a radiation beam, and typically has a transmittance of at least 10%, 25%, 50%, or 75%. In representative examples, masks include patterned beam attenuation layers or portions thereof on silicon nitride, silicon dioxide, or silicon layers of thicknesses between about 10 nm and 20 µm, typically between 10 nm and 40 nm. With sufficiently thin substrates, the beam attenuating layer need not be separated from the substrate.

Example 9. Representative Materials

The desired thickness can be based on a variety of factors such as a blocking power of the non-transmissive material and a mechanical strength of the non-transmissive material. A material for the non-transmissive areas can be selected based on a variety of factors, such as cost, mechanical strength, magnetic properties, and blocking or stopping power. Properties of suitable aperture materials can include being non-magnetic (e.g., having a low relative permeability) and having a high blocking power for electrons, such as having a high atomic number. By selecting non-magnetic materials, images can exhibit less distortion than by using magnetic materials that can deflect the CPBs transmitted by the mask. High-Z materials also permit thinner layers and tend to reduce reflections from the side-walls of transmissive areas. Suitable aperture materials can include various transition metals having atomic numbers in a range of 72 to 80. Typical examples of suitable materials include glass, gold, platinum, iridium, osmium, nickel, and copper, and combinations thereof.

The thickness of attenuating material in non-transmissive mask elements can be based on the material and a desired attenuation. As one example, the thickness can be between 30 µm and 200 µm, depending on the material. To obtain 95% blocking of 300 kV electrons, thicknesses of gold and copper of 30 µm and 80 µm, respectively, are needed. To obtain 20% transmittance, a 20 µm gold layer or a 58 µm copper layer is needed. In other examples, non-transmissive mask elements are defined by nickel in thicknesses similar to those required for copper. A glass layer about 200 µm can be used to achieve about 5% transmittance.

In one embodiment, non-transmissive mask elements are defined by a gold layer 20 µm to 40 µm thick, or a copper layer 60 µm to 90 µm thick. In some examples, thinner layers are preferred to reduce reflections from sides of the mask elements. Thicker layers provide superior mechanical strength. In some examples, a mask is mounted in a frame to provide additional structural stability.

Example 10. Computing Environment

Figure 9:
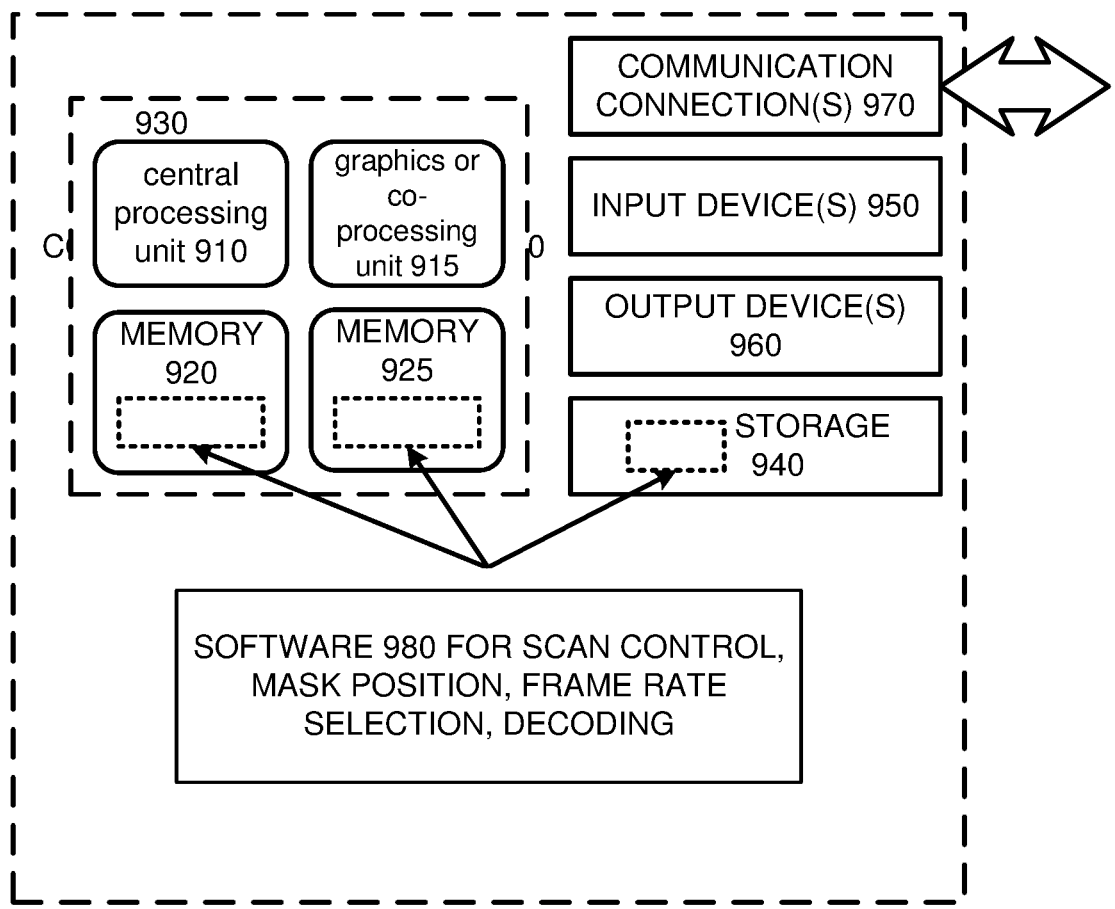
FIG. 9 is a block diagram illustrating a suitable computing environment for implementing some embodiments of the disclosed technology.

FIG. 9 depicts a generalized example of a suitable computing environment 900 in which the described innovations such as spectra and image processing, data decompression and mask pattern definition may be implemented. The computing environment 900 is not intended to suggest any limitation as to scope of use or functionality, as the innovations may be implemented in diverse general-purpose or special-purpose computing systems. For example, the computing environment 900 can be any of a variety of computing devices (e.g., desktop computer, laptop computer, server computer, tablet computer, etc.).

With reference to FIG. 9, the computing environment 900 includes one or more processing units 910, 915 and memory 920, 925. In FIG. 9, this basic configuration 930 is included within a dashed line. The processing units 910, 915 execute computer-executable instructions. A processing unit can be a general-purpose central processing unit (CPU), processor in an application-specific integrated circuit (ASIC) or any other type of processor. In a multi-processing system, multiple processing units execute computer-executable instructions to increase processing power. For example, FIG. 9 shows a central processing unit 910 as well as a graphics processing unit or co-processing unit 915. The tangible memory 920, 925 may be volatile memory (e.g., registers, cache, RAM), non-volatile memory (e.g., ROM, EEPROM, flash memory, etc.), or some combination of the two, accessible by the processing unit(s). The memory 920, 925 stores software 980 implementing one or more innovations described herein, in the form of computer-executable instructions suitable for execution by the processing unit(s).

A computing system may have additional features. For example, the computing environment 900 includes storage 940, one or more input devices 950, one or more output devices 960, and one or more communication connections 970. An interconnection mechanism (not shown) such as a bus, controller, or network interconnects the components of the computing environment 900. Typically, operating system software (not shown) provides an operating environment for other software executing in the computing environment 900, and coordinates activities of the components of the computing environment 900.

The tangible storage 940 may be removable or non-removable, and includes magnetic disks, magnetic tapes or cassettes, CD-ROMs, DVDs, or any other medium which can be used to store information in a non-transitory way and which can be accessed within the computing environment 900. The storage 940 stores instructions for the software 980 implementing one or more innovations described herein.

The input device(s) 950 may be a touch input device such as a keyboard, mouse, pen, or trackball, a voice input device, a scanning device, or another device that provides input to the computing environment 900. The output device(s) 960 may be a display, printer, speaker, CD-writer, or another device that provides output from the computing environment 900.

The communication connection(s) 970 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Alternatives and Variations

Any of the disclosed methods can be implemented as computer-executable instructions or a computer program product stored on one or more computer-readable storage media (e.g., non-transitory computer-readable media, such as one or more optical media discs such as DVD or CD, volatile memory components (such as DRAM or SRAM), or nonvolatile memory components (such as flash memory or hard drives)) and executed on a computer (e.g., any commercially available computer, including smart phones or other mobile devices that include computing hardware). By way of example and with reference to FIG. 9, computer-readable storage media include memory 920, memory 925, and/or storage 940. The term computer-readable storage media does not include signals and carrier waves. In addition, the term computer-readable storage media does not include communication connections (e.g., 970).

Any of the computer-executable instructions for implementing the disclosed techniques as well as any data created and used during implementation of the disclosed embodiments can be stored on one or more computer-readable storage media (e.g., non-transitory computer-readable media). The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

In view of the many possible embodiments to which the principles of the disclosed technology may be applied, it should be recognized that the illustrated embodiments are only preferred examples and should not be taken as limiting the scope of the disclosure. We claim all that comes within the scope of the appended claims.

We claim:

1. A method, comprising:
    combining coded spectra associated with a plurality of specimen locations based on a mask pattern and displacement modulations applied by a mask receiving generated spectrally dispersed radiation; and
    based on the combined spectra and associated encodings, determining spectra associated with each of the plurality of specimen locations.

2. The method of claim 1, wherein each of the coded spectra is associated with a different coding.

3. The method of claim 1, wherein the coded spectra are combined on a sensor and the combined coded spectra are obtained from the sensor.

4. The method of claim 1, further comprising obtaining the coded spectra by, for each of the plurality of specimen locations:
- irradiating the specimen location with a probe beam;
- spectrally dispersing radiation received from the specimen in response to the irradiation; and
- coding the spectrally dispersed received radiation with a mask.

5. The method of claim 4, wherein the coded spectra are electron energy loss spectra (EELS) and the irradiation is electron beam irradiation.

6. The method of claim 4, wherein the mask includes a plurality of linear segments arranged so that each segment is associated with different electron energy.

7. The method of claim 6, wherein each of the linear segments is associated with a first electron transmittance or a second electron transmittance.

8. The method of claim 1, further comprising summing spectral data at each specimen location so as to provide a specimen image.

9. An apparatus, comprising:
- a radiation beam scanner that selectively directs a scanned beam to a target area of a specimen;
- a mask situated to receive spectrally dispersed radiation beams responsive to respective scanned beams and generate corresponding mask-modulated, spectrally dispersed radiation beams based on relative displacements of the mask and the spectrally dispersed radiation beams; and
- a sensor situated to receive the mask-modulated, spectrally dispersed radiation beams and produce an output signal corresponding to a sum of signals associated with the mask-modulated, dispersed radiation beams.

10. The apparatus of claim 9, wherein the scanned beam is an electron beam, an x-ray beam, a gamma radiation beam, a neutron beam, an extreme ultraviolet beam, or a visible beam.

11. The apparatus of claim 10, further comprising an electron spectrometer situated to receive electron beams responsive to the scanned beams, and produce corresponding spectrally dispersed radiation beams.

12. The apparatus of claim 11, further comprising:
- a displacement stage coupled to the mask; and
- a scan controller coupled to the displacement stage and the radiation beam scanner so as to select a stage displacement associated with a scanned target area.

13. The apparatus of claim 11, further comprising:
- at least one displacement stage coupled to the mask or the sensor; and
- a scan controller coupled to the at least one displacement stage and the scan controller so as to select a stage displacement associated with a scanned target area.

14. The apparatus of claim 13, wherein the displacement stage is a piezoelectric stage.

15. The apparatus of claim 13, wherein the sensor receives at least a predetermined set of the mask-modulated, spectrally dispersed radiation beams during a sensor frame time, and produces a compressed output corresponding to a sum of signals associated with the mask-modulated, spectrally dispersed radiation beams received during the frame time.

16. The apparatus of claim 15, wherein the mask comprises a one-dimensional area of rectangular regions of a first transmittance interleaved with rectangular regions of a second transmittance that is different than the first transmittance.

17. The apparatus of claim 16, wherein the sensor is situated to receive spectral components of the mask-modulated, spectrally dispersed radiation beams along sensor pixel rows and the rectangular regions of the mask are oriented in parallel to the sensor pixel rows.

18. The apparatus of claim 11, further comprising:
- a spectral beam scanner situated so as to scan the spectrally dispersed beams with respect to the mask; and
- a scan controller coupled to the spectral beam scanner so as to select a spectral beam displacement associated with a scanned target area.

19. The apparatus of claim 18, wherein the sensor receives at least a predetermined set of the mask-modulated, spectrally dispersed radiation beams during a sensor frame time, and produces a compressed output corresponding to a sum of signals associated with the mask-modulated, spectrally dispersed radiation beams received during the frame time.

20. The apparatus of claim 19, wherein the mask comprises a one-dimensional area of rectangular regions of a first transmittance interleaved with rectangular regions of a second transmittance that is different than the first.

21. The apparatus of claim 20, wherein the sensor is situated to receive spectral components of the mask-modulated, spectrally dispersed radiation beams along sensor pixel rows and the rectangular regions of the mask are oriented in parallel to the sensor pixel rows.

22. An apparatus, comprising:
- an electron beam scanning system situated to sequentially scan a monochromatic electron beam over a selected set of specimen areas and produce corresponding electron beams having spectral components associated with energy loss;
- an electron spectrometer situated to receive the electron beams having spectral components associated with energy loss and produce corresponding spectrally dispersed beams;
- an electron beam mask situated to receive the spectrally dispersed beams with associated mask displacements and produce mask-modulated, spectrally dispersed beams based on the displaced mask patterns;
- an electron beam array sensor situated to sequentially receive the mask-modulated, spectrally dispersed beams during a sensor frame time and produce a compressed output signal corresponding to a sum of signals associated with each of the mask-modulated spectrally dispersed beams; and
- a processor coupled to receive the compressed output signal and produce spectra for each of the specimen areas of the selected set based on the compressed output signal and the mask displacements.

23. A method, comprising:
- combining coded spectra associated with a plurality of specimen locations based on a mask pattern and displacement modulations relative to a mask;
- based on the combined spectra and associated encodings, determining spectra associated with each of the plurality of specimen locations; and
- obtaining the coded spectra by, for each of the plurality of specimen locations:
  - irradiating the specimen location with a probe beam;
  - spectrally dispersing radiation received from the specimen in response to the irradiation; and
  - coding the spectrally dispersed received radiation with the mask.

24. A method, comprising:
  combining coded spectra associated with a plurality of specimen locations;
  based on the combined spectra and associated encodings, determining spectra associated with each of the plurality of specimen locations based on a mask pattern and displacement modulations relative to a mask; and
  summing spectral data at each specimen location to provide a specimen image.

25. The method of claim 23, wherein the displacement modulations relative to the mask are applied by displacement of the mask.

26. The method of claim 24, wherein the displacement modulations relative to the mask are applied by displacement of the mask.

* * * * *